United States Patent [19]

Hoercher et al.

[11] Patent Number: 4,966,734
[45] Date of Patent: Oct. 30, 1990

[54] DEODORIZATION OF FATTY ESTER MIXTURES

[75] Inventors: Ulrich Hoercher, Mannheim; Peter Lechtken, Frankenthal, both of Fed. Rep. of Germany

[73] Assignee: BASF Aktiengesellschaft, Ludwigshafen, Fed. Rep. of Germany

[21] Appl. No.: 324,044

[22] Filed: Mar. 16, 1989

[30] Foreign Application Priority Data

Apr. 23, 1988 [DE] Fed. Rep. of Germany ....... 3813805

[51] Int. Cl.$^5$ ................................................ C11B 7/00
[52] U.S. Cl. .................................... 260/420; 260/425; 426/417
[58] Field of Search ................................. 260/420, 425

[56] References Cited

U.S. PATENT DOCUMENTS 4,377,526 3/1983 Fujita et al. ......................... 260/424

FOREIGN PATENT DOCUMENTS 3226232 2/1983 Fed. Rep. of Germany .
3419796 11/1984 Fed. Rep. of Germany .

OTHER PUBLICATIONS

J. Amer. Oil Chem. Soc., Gauglitz, Jr. et al., (1963), vol. 40, pp. 197–198.
J. Amer. Oil Chem. Soc., Ke, et al., (Sep. 1975), vol. 52, pp. 349–353.
J. of Food Science, Josephson et al., (1983), vol. 48, pp. 1064–1067.

Primary Examiner—Werren B. Lone
Assistant Examiner—Vera C. Clarke
Attorney, Agent, or Firm—Oblon, Spivak, McClelland, Maier & Neustadt

[57] ABSTRACT

Undesirable odors are removed from fatty ester mixtures which, in addition to other components, contain the esters of highly unsaturated fatty acids, in particular of highly unsaturated 3-fatty acids, such as eicosapentaenoic acid or docosahexaenoic acid, by a process in which the fatty ester mixture is treated with a complex hydride, in particular with sodium borohydride solution. The process is particularly suitable for removing undesirable odors from fatty ester mixtures obtained from fish oil, for example by transesterification with an alkanol of 1 to 3 carbon atoms.

8 Claims, No Drawings

DEODORIZATION OF FATTY ESTER MIXTURES

The present invention relates to a process for removing undesirable odors from fatty ester mixtures which, in addition to other components, contain the esters of highly unsaturated fatty acids, in particular those of eicosapentaenoic acid (EPA) and docosahexaenoic acid (DHA).

The compounds EPA and DHA which belong to the group consisting of the omega-3-fatty acids have recently been disclosed as agents for preventing thrombosis and arteriosclerosis and for lowering the triglyceride level (cf. Ungesättigte Fettsäuren in der Prophylaxe und Therapie in Apothekerjournal 10 (1) (1988), 38–44 and loc. cit. 10 (2), 48–52). They occur in particular in fish oils and in the oils and fats of algae. Fish oils containing 20–30% of EPA and DHA are used for the purification of these compounds and the preparation of dietary foods. In these EPA- and DHA-containing preparations, the fatty acids may be present, inter alia, as triglycerides or as esters of lower alcohols. The alkyl esters obtained from the triglycerides by transesterification with lower alkanols have the advantage of being particularly suitable for the concentration of EPA and DHA. Processes for the transesterification of fish oils with lower alkanols and the subsequent concentration of EPA and DHA have been described in many publications (cf. E. J. Gauplitz et al in J. Amer. Oil Chem. Soc. 40 (1963), 197–198 and U.S. Pat. No. 4,377,526).

One problem in the preparation of EPA- and DHA-containing preparations from fish oils for oral consumption is the fish odor, which is extremely stubborn and remains even after transesterification and concentration of EPA and DHA. This odor is due to a large number of compounds which are formed by oxidative degradation of highly unsaturated fatty acids (cf. J. Amer. Oil Chem. Soc. 52 (1975), 349–353). These are predominantly unsaturated carbonyl compounds, which can have an intense odor even at very low concentrations. The removal of odorous substances from triglycerides is possible by deodorization with steam under reduced pressure. This process is less suitable for fatty alkyl esters, since, owing to their higher volatility, some of the esters distill over with the steam.

In many fish oil preparations, the odor and flavor problem is solved by encapsulation of the oil in soft gelatine capsules. This avoids any contact with the oil during intake. In this case too, however, an unpleasant fish flavor may be detectable subsequently (for example on repeating). Thus, regardless of the formulation chosen, it is always desirable to use an oil which has very little odor.

Another possible method for preparing odorless and tasteless fish oil preparations is the formation of cyclodextrin inclusion compounds (cf DE No. 3 226 232 and DE No. 3 419 796). This gives an odorless stable dry powder. The disadvantage of this method is that the amount to be consumed is increased by more than 100% due to the carrier.

It is an object of the present invention to provide a process for removing undesirable odors from fatty ester mixtures containing highly unsaturated fatty acids, in particular from fatty ester mixtures containing highly unsaturated omega-3-fatty alkyl esters, for example from EPA- and DHA-containing fatty alkyl ester mixtures, which does not have the disadvantages of the abovementioned known processes.

We have found that this object is achieved in that, surprisingly, deodorization of this type can be carried out in a simple manner by thoroughly stirring the ester mixture with a solution of a complex hydride, such as an aqueous sodium borohydride solution.

In this procedure, the carbonyl compounds which cause the fish odor are reduced. The decrease in the fish odor is accompanied by the appearance of a slightly fruity odor, which originates from the reduced carbonyl compounds.

The present invention therefore relates to a process for removing undesirable odors from fatty ester mixtures which, in addition to other components, contain the esters of highly unsaturated fatty acids, wherein the fatty ester mixture is treated with a complex hydride.

The process is particularly important for removing undesirable odors from fatty ester mixtures which contain esters of highly unsaturated omega-3-fatty acids, in particular of eicosapentaenoic acid and/or docosahexaenoic acid. The process can be used for mixtures which contain the highly unsaturated fatty acids as triglycerides, but is particularly important for mixtures which contain the highly unsaturated fatty acids as esters of alkanols of 1 to 3 carbon atoms, in particular for those mixtures which contain esters of highly unsaturated omega-3-fatty acids and alkanols of 1 to 3 carbon atoms. Fatty ester mixtures which are particularly advantageously used are those obtained by transesterification of fish oil with an alkanol of 1 to 3 carbon atoms, in particular those in which the esters of EPA and/or DHA have been concentrated beforehand.

According to the invention, complex metal hydrides are compounds such as lithium aluminum hydride, sodium borohydride and lithium borohydride, as well as $LiAlH[OC-(CH)_3]$ in tetrahydrofuran and diisoamylborane in tetrahydrofuran, in particular lithium aluminum hydride and sodium borohydride. The reaction with $LiAlH_4$ must be carried out in an anhydrous medium, for example in diethyl ether. $NaBH_4$ is particularly advantageously used. Since it decomposes only very slowly in water, an aqueous $NaBH_4$ solution can be used, this having considerable advantages in terms of process engineering.

The concentration of the sodium borohydride solution can be 0.01–10%, preferably 0.1–0.5%. Fish oils which are used as starting materials for preparation of the ethyl ester mixtures may have different concentrations of odorous substances, being natural products from different sources and processed in different ways. This also applies to the esters prepared therefrom. Hence, the concentration of sodium borohydride solution required to achieve the desired deodorizing effect cannot be predicted exactly, although in general 0.1–0.5% strength by weight solutions are sufficient.

From 0.1 to 5, preferably from 0.5 to 2, parts, based on the ester mixture, of sodium borohydride solution are used. The reaction temperature is 20°–60° C. The reaction mixture forms an emulsion with slight foaming. This emulsion can be broken by acidification by dilute sulfuric acid after the reaction has ended. The ester phase is then washed several times with water until the wash water is neutral. If emulsions occur during these phase separations, they can be eliminated with ethanol or sodium chloride solution.

The fatty esters treated in this manner have a fruity aromatic odor instead of a fish-like one. They can be further stabilized and formulated by any known methods, for example by the addition of antioxidants, encapsulation in soft gelatine capsules, microencapsulation or the preparation of emulsions.

The Examples which follow illustrate the invention without restricting it.

EXAMPLE 1

300 g of a fatty ethyl ester mixture obtained by transesterification of sardine oil with ethanol in the presence of sodium ethylate and containing 13% of EPA and of DHA was stirred for 30 minutes at 40° C. with 300 ml of a 0.1% strength by weight solution of sodium borohydride in water, an emulsion being formed with slight foaming. After 100 ml of 3% strength sulfuric acid had been added, the phases separated. The organic phase was washed three times with 200 ml of water, any emulsions occurring being eliminated by adding a little ethanol or sodium chloride solution. Residual water and solvents were removed by distillation at 40° C. and under 1 mbar. 295 g of an ester mixture whose fish-like odor had substantially vanished and which instead had a fruity aromatic odor were obtained.

The product was divided into two halves (A and B). Sample A was stored in an airtight container under nitrogen, whereas B was stored in contact with air. After 10 days, sample A still had the fruity odor whereas sample B had assumed a linseed oil-like odor.

EXAMPLE 2

200 g of a commercial concentrate of omega-3-fatty ethyl esters (30% of EPA and 20% of DHA) were stirred for 30 minutes at 40° C. with 200 ml of a 0.1% strength by weight sodium borohydride solution. After working up similarly to Example 1, the product had an aromatic odor.

EXAMPLE 3

6 ml of an industrial sodium borohydride solution (Ventron, 12.5% of $NaBH_4$ in 40% strength by weight sodium hydroxide solution) were diluted to 300 ml. This solution was used to carry out deodorization as described in Example 1, the same success being achieved.

EXAMPLE 4

100 g of an ethyl ester concentrate prepared by transesterification of fish oil and concentration by treatment with urea solution followed by distillation by the process according to U.S. Pat. No. 4,377,526, and containing 34% of EPA and 21% of DHA, were stirred with 100 g of a 0.25% strength by weight sodium borohydride solution for 30 minutes at 40° C., after which 100 ml of 10% strength sulfuric acid were added. After removal of the aqueous phase, washing of the ethyl ester three times with 100 ml of water and removal of residual water by distillation under reduced pressure, a product having a slightly fruity odor was obtained.

We claim:

1. A process for removing undesirable odors from a fatty ester mixture which, contains an ester of a highly unsaturated fatty acid, wherein the fatty ester mixture is treated with a complex hydride.

2. A process as claimed in claim 1, wherein the fatty ester mixture used contains the ester of a highly unsaturated omega-3-fatty acid.

3. A process as claimed in claim 1, wherein the fatty ester mixture used contains an ester of eicosapentaenoic acid (EPA) and/or docosahexaenoic acid (DHA).

4. A process as claimed in claim 1, wherein the fatty ester mixture is treated with a sodium borohydride solution.

5. A process as claimed in claim 1, wherein the mixture of esters is of highly unsaturated fatty acids and alkanols of 1 to 3 carbon atoms.

6. A process as claimed in claim 1, wherein the mixture of esters is of highly unsaturated omega-3-fatty acids and alkanols of 1 to 3 carbon atoms, and is treated with a sodium borohydride solution.

7. A process as claimed in claim 1, wherein the fatty ester mixture used has been obtained by transesterification of fish oil with an alkanol of 1 to 3 carbon atoms.

8. A process as claimed in claim 1, wherein the fatty ester mixture is one in which the esters of eicosapentaenoic acid and/or docosahexaenoic acid have been concentrated beforehand.

* * * * *